US012730828B2

(12) United States Patent
O'Brien Villate, Jr. et al.

(10) Patent No.: US 12,730,828 B2
(45) Date of Patent: Sep. 8, 2026

(54) MACHINE LEARNING BASED DATA MANAGEMENT

(71) Applicant: CVS Pharmacy, Inc., Woonsocket, RI (US)

(72) Inventors: Anthony Terrence O'Brien Villate, Jr., Brookline, MA (US); Ali Azari, Rockville, MD (US); Emily Francine Kipping, New York, NY (US)

(73) Assignee: CVS Pharmacy, Inc., Woonsocket, RI (US)

( * ) Notice: Subject to any disclaimer, the term of this patent is extended or adjusted under 35 U.S.C. 154(b) by 27 days.

(21) Appl. No.: 18/411,920

(22) Filed: Jan. 12, 2024

(65) Prior Publication Data

US 2024/0241890 A1 Jul. 18, 2024

Related U.S. Application Data

(60) Provisional application No. 63/438,985, filed on Jan. 13, 2023.

(51) Int. Cl.
*G06F 17/28* (2006.01)
*G06F 16/28* (2019.01)
*G16H 10/60* (2018.01)

(52) U.S. Cl.
CPC ........... *G06F 16/285* (2019.01); *G16H 10/60* (2018.01)

(58) Field of Classification Search
CPC .............................. G06F 16/285; G16H 10/60
USPC .......................................................... 707/737
See application file for complete search history.

(56) References Cited

U.S. PATENT DOCUMENTS 7,873,489 B2 1/2011 Dolgos et al.
8,321,044 B2 11/2012 Plahey et al.
9,269,251 B2 2/2016 Lalonde et al.
9,697,334 B2 7/2017 Yu et al.
(Continued)

FOREIGN PATENT DOCUMENTS

WO WO-96/40316 A1 12/1996
WO WO-2013/095459 A1 6/2013

OTHER PUBLICATIONS

"Patient Education: PD Overview", YouTube, Uploaded by DaVita Kidney Care, Dec. 5, 2019, https://www.youtube.com/watch?v=D_Ewhg5WJoE.

(Continued)

*Primary Examiner* — Giovanna B Colan
(74) *Attorney, Agent, or Firm* — Foley & Lardner LLP

(57) ABSTRACT

A system includes one or more memory devices having instructions stored thereon that, when executed by one or more processors, cause the one or more processors to receive data describing a plurality of patients from one or more data sources. The instructions cause the one or more processors to classify the plurality of patients into a plurality of segments describing attitudes and abilities of patients based on execution of a model trained based on a machine learning process and based on the data. The instructions cause the one or more processors to construct a database. The instructions cause the one or more processors to update the database to store classifications of the plurality of patients into the plurality of segments. The instructions cause the one or more processors to construct output data based on the classifications of the plurality of patients into the plurality of segments stored in the database.

18 Claims, 8 Drawing Sheets

(56) References Cited

U.S. PATENT DOCUMENTS

| | | | | |
|---|---|---|---|---|
| 9,760,363 | B2 | 9/2017 | Dicks et al. | |
| 10,061,899 | B2 | 8/2018 | Miller et al. | |
| 10,095,840 | B2 | 10/2018 | Miller et al. | |
| 11,260,153 | B2 | 3/2022 | Tiwari et al. | |
| 11,301,772 | B2 * | 4/2022 | Ito | G06F 16/35 |
| 11,367,532 | B2 * | 6/2022 | Hoar | A61B 5/1495 |
| 2015/0216413 | A1 * | 8/2015 | Soyao | H04L 67/12 709/204 |
| 2020/0051677 | A1 * | 2/2020 | Harrison | G06F 3/0483 |
| 2020/0053056 | A1 | 2/2020 | Mathias et al. | |
| 2021/0090694 | A1 * | 3/2021 | Colley | G16H 50/50 |
| 2021/0319887 | A1 * | 10/2021 | Derrick, Jr. | A61B 5/7275 |

OTHER PUBLICATIONS

Hazara AM, Durrans K, Bhandari S. The role of patient portals in enhancing self-care in patients with renal conditions. Clin Kidney J. 2019;13(1):1-7. Published Nov. 18, 2019. doi:10.1093/ckj/sfz154.

https://www.freseniuskidneycare.com/thriving-on-dialysis/patienthub, Webpage, Accessed Jan. 4, 2024.

https://www.freseniuskidneycare.com/treatment/home-hemodialysis/training, Webpage, Accessed Jan. 4, 2024.

https://www.glooko.com/2020/08/supporting-remote-patient-monitoring-rpm-leveraging-machine-learning-predict-dropout-risk/, Webpage Article, Accessed Jan. 4, 2024, —6 pages.

https://www.nxstage.com/hcp/training-resources/training-videos/, Webpage, Accessed Jan. 4, 2024.

https://www.pdempowers.com/patient/mybaxter, Webpage, Accessed Jan. 4, 2024.

Huang R, Liu N, Nicdao MA, Mikaheal M, Baldacchino T, Albeos A, Petoumenos K, Sud K, Kim J. Emotion sharing in remote patient monitoring of patients with chronic kidney disease. J Am Med Inform Assoc. Feb. 1, 2020;27(2):185-193. doi: 10.1093/jamia/ocz183. PMID: 31633755; PMCID: PMC7647270.

Liu, N., Kim, J., Jung, Y., Arisy, A., Nicdao, M. A., Mikaheal, M., Baldacchino, T., Khadra, M., & Sud, K. (2017). Remote Monitoring Systems for Chronic Patients on Home Hemodialysis: Field Test of a Copresence-Enhanced Design. JMIR human factors, 4(3), e21. https://doi.org/10.2196/humanfactors.7078.

Machine Learning for Prediction of Patients on Hemodialysis with an Undetected SARS-CoV-2 Infection; Caitlin K. Monaghan, John W. Larkin, Sheetal Chaudhuri, Hao Han, Yue Jiao, Kristine M. Bermudez, Eric D. Weinhandl, Ines A. Dahne-Steuber, Kathleen Belmonte, Luca Neri, Peter Kotanko, Jeroen P. Kooman, Jeffrey L. Hymes, Robert J. Kossmann, Len A. Usvyat, Franklin W. Maddux; Kidney360 Mar. 2021, 2 (3) 456-468; DOI: 10.34067/KID.0003802020.

Sheng K, Zhang P, Yao X, Li J, He Y, Chen J; Prognostic Machine Learning Models for First-Year Mortality in Incident Hemodialysis Patients: Development and Validation Study; JMIR Med Inform 2020;8(10): e20578; URL: https://medinform.jmir.org/2020/10/e20578; DOI: 10.2196/20578.

Wallace EL, Rosner MH, Alscher MD, et al. Remote Patient Management for Home Dialysis Patients. Kidney Int Rep. 2017;2(6):1009-1017. Published Jul. 29, 2017. doi:10.1016/j.ekir.2017.07.010.

Vinik, Danny. Obama's Effort To Nudge America. Politico, Oct. 15, 2015, www.politico.com/agenda/story/2015/10/obamas-effort-to-nudge-america-000276/.

* cited by examiner

300

| 125 | SEGMENT 1 Independent and Capable (150) | SEGMENT 2 Support-Seeking and Engaged (150) | SEGMENT 3 Struggling and Detached (150) | SEGMENT 4 Depressed but Involved (150) |
| --- | --- | --- | --- | --- |
| CLINICAL CAPACITY<br>• Outlook<br>• Ability & Support<br>• Health Literacy | **HIGH** | MEDIUM | **LOW** | MEDIUM |
| HEALTH ENGAGEMENT<br>• Goal-Oriented<br>• Engagement Levels<br>• Adherence Levels | MEDIUM | **HIGH** | **LOW** | **HIGH** |
| HEALTH STATUS*<br>• Number of Conditions<br>• Claims History | MEDIUM | MEDIUM | **LOW** | **LOW** |
| Access<br>• Access to tech Devices<br>• Access to Basic Needs | **HIGH** | **LOW** | MEDIUM | MEDIUM |

FIG. 3

MACHINE LEARNING BASED DATA MANAGEMENT

CROSS-REFERENCE TO RELATED PATENT APPLICATION

This application claims the benefit of and priority to U.S. Provisional Application No. 63/438,985 filed on Jan. 13, 2023, the entire disclosure of which is incorporated by reference herein.

BACKGROUND

The present disclosure relates generally to systems that implement machine learning processes and machine learning models. A computer system can implement machine learning processes to train a machine learning model. The computer system can execute the model with an inference process to generate an output based on an input dataset. Machine learning can include supervised learning or unsupervised learning.

SUMMARY

One implementation of the present disclosure is a system including one or more memory devices having instructions stored thereon, that, when executed by one or more processors, cause the one or more processors to receive data describing patients from one or more data sources. The instructions cause the one or more processors to classify the patients into segments describing attitudes and abilities of patients based on execution of a model trained based on a machine learning process and based on the data. The instructions cause the one or more processors to construct a database. The instructions cause the one or more processors to update the database to store classifications of the patients into the segments. The instructions cause the one or more processors to construct output data based on the classifications of the patients into the segments stored in the database.

In some examples, the instructions cause the one or more processors to generate a training data set based on the data, the training data set including sets of the data for a portion of the patients and segments that the portion of the patients are classified into. In some examples, the instructions cause the one or more processors to train the model by execution of the machine learning process on the training data set.

In some examples, the instructions cause the one or more processors to select a software application from software applications for a patient based on a segment that the model classified the patient into, generate at least one credential for the patient to access the software application, construct a message to access the software application, the message including the credential or a link to accessing the software application with the credential, and transmit the message to a device of the patient.

In some examples, the instructions cause the one or more processors to retrieve, from the database, a classification of a first patient of the patients into a first segment of the segments, retrieve, from the database, a classification of a second patient of the patients into a second segment of the segments, generate first output data for the first patient based on the classification of the first patient into the first segment, and generate second output data for the second patient based on the classification of the second patient into the second segment, wherein the first output data is different than the second output data.

In some examples, the instructions cause the one or more processors to retrieve, from the database, a classification of a patient of the patients into a segment of the plurality of segments, select at least one software application for the patient from the database, the software application linked to the segment, generate the output data to provide the patient access to the software application, and transmit the output data to a device of the patient.

In some examples, the instructions cause the one or more processors to execute a second machine learning process based on the data to identify a level that features of the data stored in the database predict a goal, identify a portion of the features associated with levels greater than a threshold, and construct the segments based on the portion of the features.

In some examples, the instructions cause the one or more processors to construct the database to include a plurality of sections, save first data of the data describing the plurality of patients in a first section of the plurality of sections linked to a first segment of the plurality of segments, and store at least one identifier of the first segment in the database to label the first data stored in first section. The instructions cause the one or more processors to save second data of the data describing the plurality of patients in a second section of the plurality of sections linked to a second segment of the plurality of segments and store at least one identifier of the second segment in the database to label the second data stored in first section.

In some examples, the instructions cause the one or more processors to receive a request to generate an output for patients classified into the first segment, query the database based on the identifier for the first segment, receive the first data responsive to the query, and execute an operation to generate the output for the patients based on the first data received from the database.

In some examples, the segments describe dimensions including a clinical capacity dimension indicating an attitude of patients towards medical care and an ability of the patients to receive the medical care, a health engagement dimension indicating an ability of the patients to engage with the medical care, a health status dimension indicating existing medical conditions of the patients, and an access dimension indicating a level of access the patients have to resources.

In some examples, the clinical capacity dimension includes factors including a positive or negative outlook on life, a level of ability and support, and a level of literacy regarding medical treatments or conditions.

In some examples, the health engagement dimension includes factors including a level of a goal-oriented characteristic of the patients, an engagement level of the patients with medical treatments, and a level of adherence to a medical treatment plan.

In some examples, the health status dimension includes factors including a number of conditions that a patient has and a number of medical claims made for the patient.

In some examples, the access dimension includes factors including a level to access of the patients to technological devices and a level of access of the patients to basic needs.

In some examples, a first portion of the patients classified into an independent and capable segment of the segments are associated with the clinical capacity dimension greater than a first threshold. In some examples, a second portion of the patients classified into a support-seeking and engaged segment of the segments are associated with the clinical capacity dimension less than the first threshold and greater than second threshold. In some examples, a third portion of the patients classified into a struggling and detached segment of the segments are associated with the clinical capacity dimension less than the second threshold. In some examples, a fourth portion of the patients classified into a depressed but involved segment of the segments are associated with the clinical capacity dimension less than the first threshold and greater than the second threshold.

In some examples, a first portion of the patients classified into an independent and capable segment of the segments are associated with the health engagement dimension less than a first threshold and greater than a second threshold. In some examples, a second portion of the patients classified into a support-seeking and engaged segment of the segments are associated with the health engagement dimension greater than the first threshold. In some examples, a third portion of the patients classified into a struggling and detached segment of the segments are associated with the health engagement dimension less than the second threshold. In some examples, a fourth portion of the patients classified into a depressed but involved segment of the segments are associated with the health engagement dimension greater than the first threshold.

In some examples, a first portion of the patients classified into an independent and capable segment of the segments are associated with the health status dimension less than a first threshold and greater than a second threshold. In some examples, a second portion of the patients classified into a support-seeking and engaged segment of the segments are associated with the health status dimension less than the first threshold and greater than the second threshold. In some examples, a third portion of the patients classified into a struggling and detached segment of the segments are associated with the health status dimension less than the second threshold. In some examples, a fourth portion of the patients classified into a depressed but involved segment of the segments are associated with the health status dimension less than the second threshold.

In some examples, a first portion of the patients classified into an independent and capable segment of the segments are associated with the access dimension greater than a first threshold. In some examples, a second portion of the patients classified into a support-seeking and engaged segment of the segments are associated with the access dimension less than a second threshold. In some examples, a third portion of the patients classified into a struggling and detached segment of the segments are associated with the access dimension less than the first threshold and greater than the second threshold. In some examples, a fourth portion of the patients classified into a depressed but involved segment of the segments are associated with the access dimension less than the first threshold and greater than the second threshold.

Another implementation of the present disclosure is directed to a method. The method can include receiving, by one or more processing circuits, data describing a plurality of patients from one or more data sources. The method can include classifying, by the one or more processing circuits, the plurality of patients into a plurality of segments describing attitudes and abilities of patients based on execution of a model trained based on a machine learning process and based on the data. The method can include constructing, by the one or more processing circuits, a database. The method can include updating, by the one or more processing circuits, the database to store classifications of the plurality of patients into the plurality of segments. The method can include constructing, by the one or more processing circuits, output data based on the classifications of the plurality of patients into the plurality of segments stored in the database.

In some examples, the method can include generating, by the one or more processing circuits, a training data set based on the data. The training data set can include a plurality of sets of the data for a portion of the plurality of patients and segments that the portion of the plurality of patients are classified into. The method can include training, by the one or more processing circuits, the model by execution of the machine learning process on the training data set.

In some examples, the method can include selecting, by the one or more processing circuits, a software application from a plurality of software applications for a patient based on a segment into which the model classified the patient. The method can include generating, by the one or more processing circuits, at least one credential for the patient to access the software application. The method can include constructing, by the one or more processing circuits, a message to access the software application, the message comprising the credential or a link to accessing the software application with the credential. The method can include transmitting, by the one or more processing circuits, the message to a device of the patient.

In some examples, the method can include retrieving, by the one or more processing circuits, from the database, a classification of a first patient of the plurality of patients into a first segment of the plurality of segments. The method can include retrieving, by the one or more processing circuits, from the database, a classification of a second patient of the plurality of patients into a second segment of the plurality of segments. The method can include generating, by the one or more processing circuits, first output data for the first patient based on the classification of the first patient into the first segment. The method can include generating, by the one or more processing circuits, second output data for the second patient based on the classification of the second patient into the second segment, wherein the first output data is different than the second output data.

In some examples, the method can include retrieving, by the one or more processing circuits, from the database, a classification of a patient of the plurality of patients into a segment of the plurality of segments. The method can include selecting, by the one or more processing circuits, at least one software application for the patient from the database, the software application linked to the segment. The method can include generating, by the one or more processing circuits, the output data to provide the patient access to the software application. The method can include transmitting, by the one or more processing circuits, the output data to a device of the patient.

In some examples, the method can include executing, by the one or more processing circuits, a second machine learning process based on the data to identify a level that features of the data stored in the database predict a goal. The method can include identifying, by the one or more processing circuits, a portion of the features associated with levels greater than a threshold. The method can include constructing, by the one or more processing circuits, the plurality of segments based on the portion of the features.

In some examples, the method can include constructing, by the one or more processing circuits, the database to include a plurality of sections. The method can include saving, by the one or more processing circuits, first data of the data describing the plurality of patients in a first section of the plurality of sections linked to a first segment of the plurality of segments. The method can include storing, by the one or more processing circuits, at least one identifier of the first segment in the database to label the first data stored in the first section. The method can include saving, by the one or more processing circuits, second data of the data describing the plurality of patients in a second section of the plurality of sections linked to a second segment of the plurality of segments. The method can include storing, by the one or more processing circuits, at least one identifier of the second segment in the database to label the second data stored in the second section.

In some examples, the method can include receiving, by the one or more processing circuits, a request to generate an output for patients classified into the first segment. The method can include querying, by the one or more processing circuits, the database based on the identifier for the first segment. The method can include receiving, by the one or more processing circuits, the first data responsive to the query. The method can include executing, by the one or more processing circuits, an operation to generate the output for the patients based on the first data received from the database.

Another implementation of the present disclosure is one or more storage media having instructions stored thereon, that, when executed by one or more processors, cause the one or more processors to receive data describing a plurality of patients from one or more data sources. The instructions can cause the one or more processors to classify the plurality of patients into a plurality of segments describing attitudes and abilities of patients based on execution of a model trained based on a machine learning process and based on the data. The instructions can cause the one or more processors to construct a database. The instructions can cause the one or more processors to update the database to store classifications of the plurality of patients into the plurality of segments. The instructions can cause the one or more processors to construct output data based on the classifications of the plurality of patients into the plurality of segments stored in the database.

In some examples, the instructions can cause the one or more processors to generate a training data set based on the data. The training data set can include a plurality of sets of the data for a portion of the plurality of patients and segments that the portion of the plurality of patients are classified into. The instructions can cause the one or more processors to train the model by execution of the machine learning process on the training data set.

In some examples, the instructions can cause the one or more processors to select a software application from a plurality of software applications for a patient based on a segment into which the model classified the patient. The instructions can cause the one or more processors to generate at least one credential for the patient to access the software application. The instructions can cause the one or more processors to construct a message to access the software application, the message comprising the credential or a link to accessing the software application with the credential. The instructions can cause the one or more processors to transmit the message to a device of the patient.

In some examples, the instructions can cause the one or more processors to execute a second machine learning process based on the data to identify a level that features of the data stored in the database predict a goal. The instructions can cause the one or more processors to identify a portion of the features associated with levels greater than a threshold. The instructions can cause the one or more processors to construct the plurality of segments based on the portion of the features.

This summary is illustrative only and should not be regarded as limiting. All examples and features mentioned above can be combined in any technically possible way.

BRIEF DESCRIPTION OF THE DRAWINGS

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

FIG. 3 is a table of example patient segments and values for each patient segment for dimensions of the patient data.

DETAILED DESCRIPTION

Figure 1:
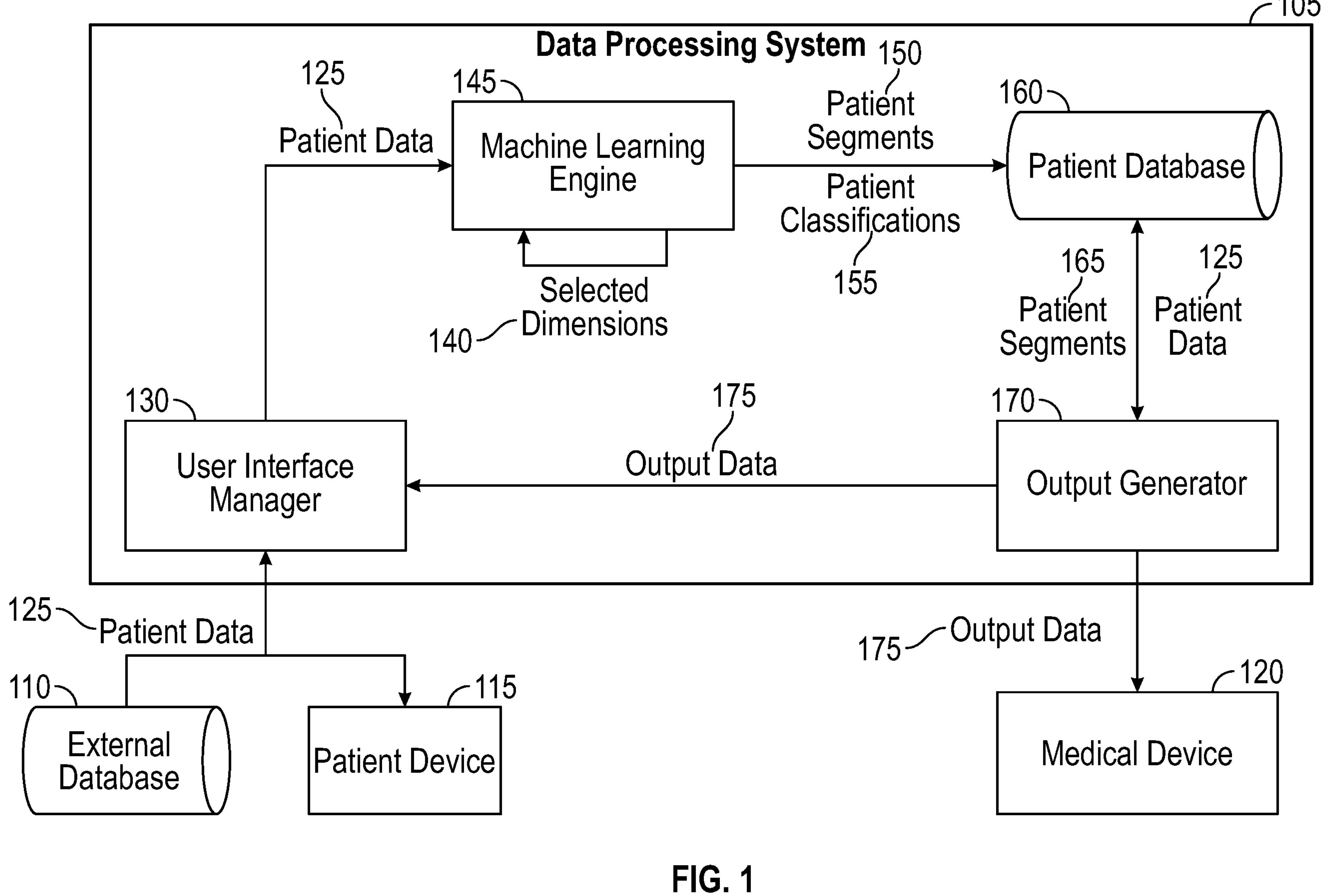
FIG. 1 is block diagram of an example data processing system that segments patient data based on machine learning.

Referring generally to the FIGURES, systems and methods are described for classifying patients into patient segments based on machine learning. A data processing system can be configured to receive patient data describing characteristics of patients, e.g., health data, technology access, age, demographics, and a variety of other characteristics. The data processing system can execute at least one computer process to perform machine learning to generate and train a model that classifies patients identified in the patient data into at least one of a set, group, or collection of segments. The model can be a multi-class model that outputs a probability of a patient being classified into each of the segments. The model can predict a segment to which a patient most likely belongs. Based on the classifications of the patients into segments, the data processing system can organize the patient data. For example, the data processing system can construct a database and store the patient data in the database that organizes the patient data into segments identified for the patients by the model trained based on machine learning.

Some data processing systems can receive unclassified patient data and attempt to generate outputs, commands, decisions, or other data to take actions for the patients. For example, a model, process, machine learning model, artificial intelligence module, or software module, can consume patient data and generate a personalized message to increase patient engagement and response to a medical treatment that the patient is receiving. However, without segmentation of the patient data, the data processing systems may encounter various problems, for example, if the data processing system uses a machine learning model to generate the outputs, if there are an excessive amount of dimensions for the machine learning model to consider, the machine learning model may be a significant size and require a significant amount of data storage resources, processing resources, and power resources to execute. To avoid consuming significant memory or storage resources, the techniques described herein can classify and segment the patient data. By classifying and segmenting the patient data, a machine learning model that determines outputs based on the patient data can consider the segments as an input to the machine learning model which can enable the machine learning model to generate accurate outputs without requiring the machine learning model to consume excessive storage and computational resources.

The techniques described herein can include identifying segments that are meaningfully differentiated based on certain attitudes and behaviors that can help tactically inform a service experience. Patients can be differentiated across a variety of factors that show distinct nuances in needs, attitudes, and behaviors. The techniques described herein can develop strategies to cause patients to convert, continue medical treatment, or prevent treatment dropout based on the segments that the patients are classified into. Because the strategies can be generated based on segments, patients may be receptive and responsive to services since the services may be specific to the patient. The services can include tools that encourage behavior change to, or adopt, virtual or non-virtual interventions.

This personalization of messaging or services can include technical challenges. For example, a system that does not have patients classified into segments may have difficulty in personalizing messages or services. However, because the systems discussed herein classify patients into segments, the data processing system can improve the graphical user interfaces displayed to users by providing information or service suggestions that the patients are most likely to engage in.

Referring now to FIG. 1, an example data processing system 105 configured to segment patient data 125 based on machine learning is shown. The data processing system 105 can be configured to receive the patient data 125 from an external database 110 or a patient device 115. The patient data 125 can include dimensions, data elements, features, parameters, or indications of characteristics of a patient. The patient data 125 can be timeseries data, categorical data, text string data, binary data, value data, etc. The patient data 125 can be collected from an external database 110 or received from a patient device 115, e.g., a smartphone, a telephone, a tablet, a laptop, a computer, a desktop computer, etc. The patient data 125 can be determined, derived, or extracted from patient records, patient survey answers, public data, or patient specified information. In some examples, the patient data 125 is a portion, percentage, or amount of a larger patient data set. The patient data 125 could be 4-6% of at risk or highest risk patients, 3-7% of at risk or highest risk patients in a patient dataset, less than 4% of at risk or highest risk patients in a patient data set, or more than 7% of at risk or highest risk patients in a patient data set. The patient data 125 can describe general attitudes of patients, healthcare attitudes of patients, stated behaviors of patients, demographic information of patients, claim data of patients, etc. Patients can be individuals that are receiving medical care, have received medical care in the past, or may receive medical care in the future. The patients can be members belonging to a health service, individuals subscribed to a newsletter or email distribution, etc.

The data processing system 105 can include a user interface manager 130. The user interface manager 130 can be configured to generate data to cause the patient device 115 to display a graphical user interface. The graphical user interface can prompt patients to enter patient data 125. Furthermore, the user interface manager 130 can display output data 175 to the patient. The output data 175 can be a graphical user interface or message that is based on a patient segment 165 assigned to the patient. The user interface manager 130 can transmit or receive text messages, mobile application data, web page data, or other information. The user interface manager 130 can further place phone calls with the patient device 115, receive spoken input from the patient device 115, or receive phone key presses from the patient device 115.

For example, the user interface manager 130 can conduct a survey by transmitting prompts, questions, or queries to the patient device 115 and receiving responses, inputs, or other patient data 125 from the patient device 115. The user interface manager 130 can conduct a survey of 5% of at risk or highest risk patients to collect the patient data 125 for the patients. The data processing system 105 could place an automated phone call to the patient devices 115 of the patients and collect the patient answers. The data processing system 105 can transmit a message or messages, e.g., emails, instant messages, text messages, or application-based messages, to collect the patient answers. The survey can collect patient data 125 that indicates or captures attitudes, behaviors, or preferences of the patients. The survey can be or include a questionnaire that incorporates at least one or multiple dimensions 140. The dimensions 140 can indicate patient outlooks, patient personalities, resources available to the patients, patient demographics, etc. The patient data 125 can be collected for a group, set, or population of patients or for specific cohorts or populations of patients, e.g., patients receiving home healthcare, patients with chronic kidney disease (CKD), or other medical conditions, etc.

The survey can identify general patient attitudes, patient attitudes to health care, attitudes to at home kidney dialysis or other medical treatments, patient demographic data, patient socioeconomic factors. The general attitudes can explore a patient's outlook on life, their ambitions, their relationships, etc. The general attitudes can allow the data processing system 105 to realize relationships and underlying dynamics of patients. The survey can identify healthcare attitudes that allow the data processing system 105 to understand a patient's role in their own health and the patients sentiment towards healthcare. The healthcare attitudes can allow the data processing system 105 to uncover existing relationships and dynamics between patients and healthcare providers, caregivers, etc. The healthcare attitudes can allow the data processing system 105 to confirm or discover any existing conditions or comorbidities that patients suffer from. The patient attitudes to at home kidney dialysis (or other medical treatments) can explore familiarity, understanding, and perceptions as it relates to kidney disease and treatment (or other medical conditions and treatments). The demographics can capture demographic information. The socioeconomic factors can indicate patient communication preferences and allow the data processing system 105 to understand which social determinants of health (SDoH) elements are most influential.

One dimension 140 can indicate a patient's outlook on life. The patient's outlook on life can indicate a value range or spectrum of values from defeated to hopeful. The patient's outlook on life can indicate a value in a range or spectrum of values for sole responsibility to a greater purpose. The patient's outlook on life can indicate mental health or depression. The patient's outlook on life can indicate emotional wellness. One dimension 140 can indicate a decision-making ability of a patient. The decision-making ability of the patient can indicate a value in a range or spectrum from decision maker to advice follower. The decision-making ability of the patient can indicate a value in a range or spectrum from struggling to empowered.

One dimension 140 can indicate health engagement of a patient. The health engagement of the patient can indicate a value in a range or spectrum from passive to active. The health engagement of the patient can indicate a value in a range or spectrum from reactive to proactive. The health engagement of the patient can indicate a value in a range or spectrum of comfort level with self-treatment. The health engagement can indicate a value in a range or spectrum from low to high for interest in health care. One dimension 140 can indicate health literacy of a patient. The health literacy can indicate a value in a range or spectrum from illiterate to literate. The health literacy can indicate a value indicating education or knowledge of chronic kidney disease or other medical conditions.

One dimension 140 can indicate a relationship of the patient with a healthcare provider. The dimension 140 can indicate a value in a range or spectrum from superficial to an intimate relationship with the healthcare provider. The dimension 140 can indicate a comfort level with the healthcare provider. The dimension 140 can indicate feelings or a sentiment towards the health care provider. The dimension 140 can indicate a source of trust in health care information. One dimension can indicate a level of social support of a patient. The dimension 140 can indicate a value in a range or spectrum from lacking support to a strong support system.

One dimension 140 can indicate socio-economic factors and SDoH. The dimension 140 can indicate financial status, race or ethnicity, employment status, education level, income level, access to transportation, access to food, security, or education. One dimension 140 can include attitudes towards chronic kidney disease, or other medical conditions. For example, the dimension 140 can indicate beliefs around kidney disease, duration of kidney disease, familiarity with dialysis, whether the patient is seeking a kidney transplant, and a patient's sentiment towards in-home kidney dialysis. While kidney disease is one example of a disease for which the technology in this disclosure could be applicable, it should be appreciated that the technology described herein may be incorporated or utilized for other diseases or medical conditions. One dimension 140 can be a demographics dimension. The dimension 140 can indicate patient age, gender, additional demographics, price sensitivity, or comfort level with technology.

The survey can prompt patients to answer questions that belong to one or multiple different patient populations. Furthermore, the survey can target a percentage of patients that belong to the different patient populations. For example, one population can be a population of patients receiving home healthcare, e.g., patients that are receiving healthcare from a medical device 120 located in their home, e.g., an at home hemodialysis apparatus. The survey can target a top five percent of patients in the home health care population based on a strategic stratification score. The top five percent of patients can include patients diagnosed with CKD (or a high risk of CKD) or patients that are not diagnosed with CKD. The patients can be male or female. The patients can be under 65 years old, 65-74 years old, or 75 years or older. The patients can have cardiovascular disease, cardiac heart failure, chronic obstructive pulmonary disease (COPD), diabetes, obesity, anxiety, depression, or other medical conditions.

Another population could be a population based on the type of care a patient is receiving, e.g., patients that are receiving kidney care, hemodialysis, etc. either at home, at a care center, or a hospital. The patients of the population can be identified by a model as being those that currently (or identified as high risk for being diagnosed with) have a certain stage of CKD, e.g., stage 3 CKD or above. The patients can be male or female. The patients can be under 65 years old, 65 years old to 74 years old, or older than 75 years old. The patients can have comorbidities such as cardiovascular disease, cardiac heart failure, COPD, diabetes, obesity, anxiety, or depression. The patients can have CKD stages 1 to 2, stage 3, stage 4, stage 5, stage 6 (end stage renal disease (ESRD)), or patients with a history of hemodialysis within a previous time window (e.g., within the last twelve months). The survey can target CKD stages and weight a final output based on the number of patients in each CDK stage.

The data processing system 105 can include a machine learning engine 145. The machine learning engine 145 can construct, train, or execute one or multiple models. For example, the machine learning engine 145 can perform supervised or unsupervised learning to train a model to classify patients based on the patient data 125 into at least one patient segment 150. The machine learning engine 145 can execute one or multiple analysis models or machine learning processes to identify dimensions 140 in the patient data 125. In some cases, the dimensions 140 are provided to the machine learning engine 145 with the patient data 125. For example, the patient data 125 can correspond to dimensions 140 learned by the machine learning engine 145 or received by the machine learning engine 145. By running on the patient data 125 clustered into the various dimension 140, which can indicate attitudinal aspects that drive classification into the patient segments 150, the machine learning engine 145 can generate patient classifications 155 in the patient segments 150 accurately and efficiently, e.g., without consuming excessive memory storage or computational resources. In some cases, the machine learning engine 145 can classify the patients into the patient segments 150 based on attitudinal dimensions instead of clinical or demographic variables. In some cases, the machine learning engine 145 can classify the patients into the patient segments 150 based on attitudinal dimensions, clinical dimensions, and/or demographic variables.

The machine learning engine 145 can train, test, or execute a model to generate patient classifications 155 for each of the patients. The patient classifications 155 can assign a patient into one of the patient segments 150 based on the patient data 125 for the patient being classified. The machine learning engine 145 can train, test, or execute a neural network, such as a convolutional neural network, a recurrent neural network, or any other type of neural network. The machine learning engine 145 can train, test, or execute a gradient boost model, an XGboost model, a Bayesian model, a hierarchical Bayesian model, a decision tree, a Gaussian model, a support vector machine (SVG), and/or any other type of supervised or unsupervised model.

The machine learning engine 145 can store the patient classifications 155 into the patient database 160. The machine learning engine 145 can construct, build, or generate the patient database 160 and modify or update the patient database 160 to store records identifying each patient, the patient segment 150 that each patient is classified into, and the patient data 125 for the patient. The patient database 160 can be segmented or divided into portions, each portion storing patient data 125 for patients classified into one patient segment 150. The patient records of the patient database 160 can be tagged based on the patient classifications 155. In some cases, the machine learning engine 145 can be a non-machine learning engine. The machine learning engine 145 can perform classification via a piece of classification software, a classification module, or a classification executable that does not implement machine learning.

The data processing system 105 can include an output generator 170. The output generator 170 can communicate with the patient database 160. For example, the output generator 170 can query the patient database 160 for patient data 125 of patients belonging to a particular patient segment 165. For example, the output generator 170 can generate query data, e.g., a request for patients of a particular patient segment 165. The request can include parameters that define the searched for patients. The parameters can identify the patient segment or segments 165 that the output generator 170 is searching for, demographic data, age data, medical conditions, or any other value, category, or state of patient data 125 that the output generator 170 is searching for.

Because the patient database 160 can include patients with taggable patient segments 150, the output generator 170 can select, view, or identify patient groups based on the tags of the patient database 160 for particular patients. The taggable patient data of the patient database 160 can provide an actionable segmentation solution to enable the output generator 170 to identify and find patients to push actions, messages, software, etc. to patients. The patient database 160 can be segmented, partitioned, or split into multiple storage areas. In some examples, the machine learning engine 145 can generate a storage region of the patient database 160 for each patient segment 150 that the machine learning engine 145 generates or receives. The machine learning engine 145 can split the patient data 125 into multiple different groups such that the patient data for patients classified into each patient segment 150 are grouped together. Each group of data can be stored in the corresponding storage section of the patient database 160 along with at least one identifier, label, or name of the corresponding patient segment 150. The output generator 170 can query the patient database 160 for a particular group of patient data with an identifier of a patient segment 150, e.g., responsive to receiving a request to generate the output data 175 for the patient segment 150. The patient database 160 can provide the data corresponding to the identifier of the patient segment 150 by retrieving the patient data from the storage area associated with the identifier of the patient segment 150. The patient database 160 can provide the retrieved data to the output generator 170. The output generator 170 can receive the retrieved data from the patient database 160.

The patient database 160 can respond to the output generator 170 with the patient data 125. For example, the patient database 160 can identify patients and corresponding patient data 125 for the patients that meet at least one criteria defined by the query data of the output generator 170. The patient database 160 can transmit the patient data 125 to the output generator 170. The output generator 170 can execute at least one application, artificial intelligence module, rule engine, model trained by machine learning, algorithm, computer executable, etc. to generate output data 175. The output data 175 can be a prediction of a clinical outcome for a patient or patients. The output data 175 can cause a system to generate, select, or identify messages, notifications, text messages, emails, or any other piece of information. For example, the output generator 170 can generate messages based on a predicted patient outcome. The message could be an intervention to help avoid a predicted patient outcome, e.g., a reminder to continue treatment if the patient's predicted outcome is to stop treatment. The output generator 170 can generate, select, or identify the messages based on the patient segments 165 or the patient data 125. Because the patient database 160 indicates the patient segments 165 for each patient, the output generator 170 can generate personalized messaging which can increase member response and engagement. This can improve outcomes for various patients.

The output generator 170 can provide the output data 175 to the user interface manager 130 to be delivered to the patient device 115 as a notification, an email, a text message, or an element in a graphical user interface. The output generator 170 can provide the output data 175 to a medical device 120. The medical device 120 can be a hospital computer system, a care center computer system, an at home medical device or apparatus, an at home hemodialysis apparatus, a hospital or care center hemodialysis apparatus. The output data 175 can cause the medical device 120 to display information on a display of the medical device 120. The output data 175 can set operating parameters, settings, or other conditions of the medical device. For example, the output data 175 can set a length of time for a treatment, e.g., a length of time for hemodialysis to be performed for a patient. The output data 175 can set a flow rate at which blood is removed or returned to a body for a patient.

The output generator 170 can select software applications for patients based on the segments 150 that the patients are classified into. For example, different software applications can provide services, information, or features that aid patients in specific segments 150. The output generator 170 can select a software application corresponding to a segment 150 of a particular patient. The output generator 170 can generate an access credential, e.g., a temporary or permanent access credential to allow the patient to login to the software application, download the software application, or otherwise access the software application. The output generator 170 can generate a message for the patient that includes the access credential or a link that accesses the software application with the access credential. The output generator 170 can deliver the message to the patient device 115 associated with the patient.

Figure 2:
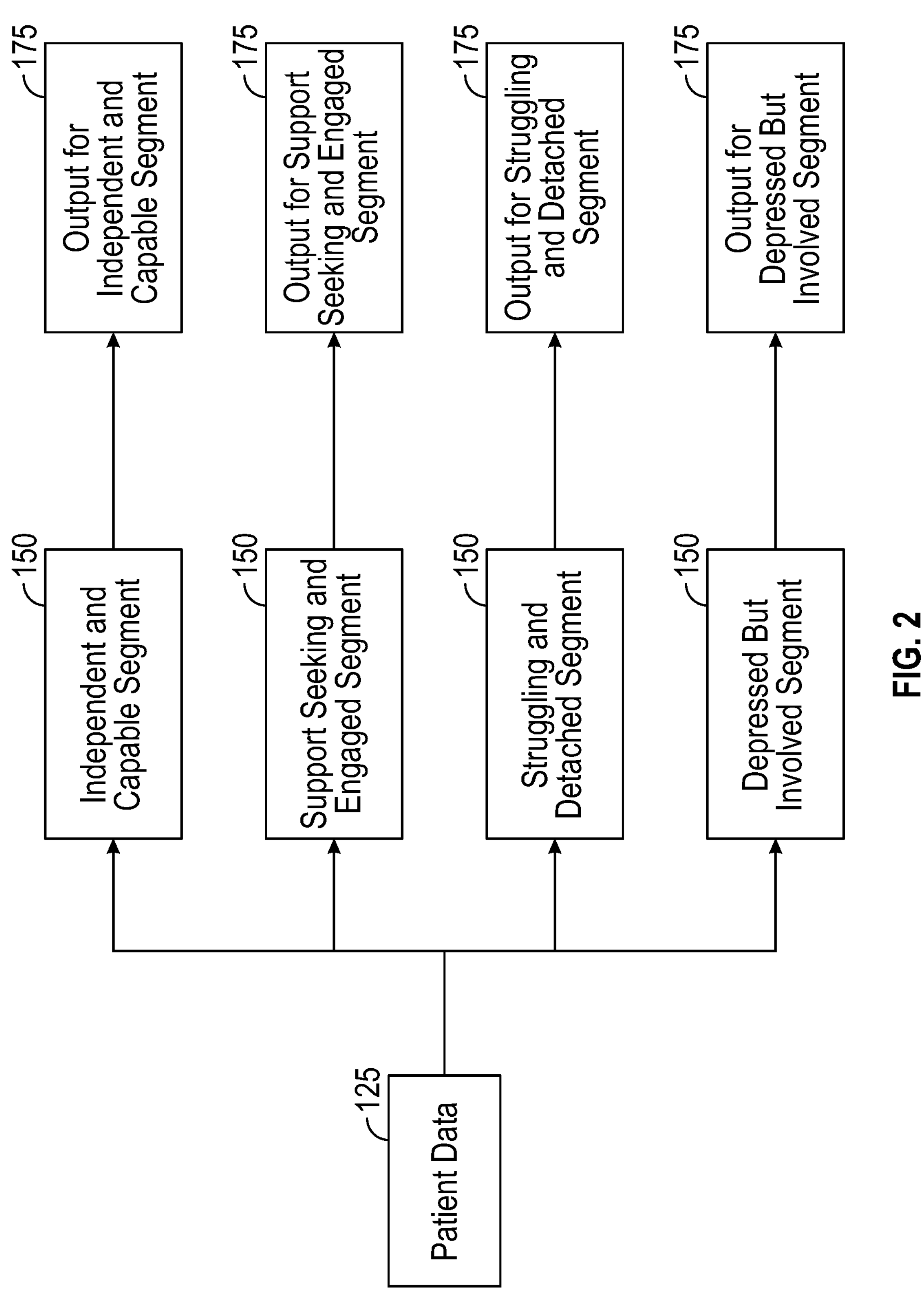
FIG. 2 is a block diagram of example patient segments where a machine learning engine classifies patients into the patient segments based on patient data.

Referring now to FIG. 2, a block diagram of example patient segments 150 where a machine learning engine 145 classifies patients into the patient segments 150 based on the patient data 125 is shown. The patient segments 150 can include an independent and capable segment 150, a support seeking and engaged segment 150, a struggling and detached segment 150, and a depressed but involved segment 150. Based on the patient segments 150 and/or the patient data 125, the output generator 170 can generate output data 175. Each segment 150 can generate a specific type or group of output data 175.

The independent and capable segment 150 can define patients that are confident, capable, and engaged. Patients classified in the independent and capable segment 150 can be less overwhelmed and less likely to seek support and guidance from other patients. Patients classified in the independent and capable segment 150 can have little trouble understanding health information and least difficulty with self-care. Many of these patients may engage in healthy behaviors and seek out information on their own. Patients classified in the independent and capable segment 150 can have fewer conditions, are older, more educated, have a higher income and are least concerned with access to basic needs. Medical costs per person are lowest among patients classified in the independent and capable segment 150.

For a medical provider, the output data 175 for the independent and capable segment 150 can include offering digital tools that help the patients of the independent and capable segment 150 feel empowered and in-control, but also connected to their provider, such as on-demand virtual services and health tracking tools. As patients in the independent and capable segment 150 are already doing well, there may be little opportunity to further decrease costs and/or increase engagement for patients in the independent and capable segment 150. The output data 175 can offer digital tools and/or health tracking benefits to nudge or remind patients classified in the independent and capable segment 150 towards regular healthier behaviors.

Patients classified in the support seeking and engaged segment 150 can be extremely engaged but in need of support. Patients in the support seeking and engaged segment 150 can be hopeful, confident, and goal-oriented. Patients in the support seeking and engaged segment 150 may have less trouble understanding health information, but may expresses difficulty with self-care. Patients in the support seeking and engaged segment 150 can spend time with others, look for guidance, and need social support. However, patients in the support seeking and engaged segment 150 also engage in healthy behaviors and seek out information, while following doctors' orders as closely as possible. Patients in the support seeking and engaged segment 150 may be more diverse, less educated, less tech-enabled, and most concerned with access to basic needs.

The output data 175 for the support seeking and engaged segment 150 can include offering regular, empathetic in-person guidance and education to address questions and concerns. Providing SDOH services can reduce barriers to resources and support holistic health. The output for the support seeking and engaged segment 150 can include expanding access to SDOH services and driving awareness of educational resources to help this group feel more at ease and in control of their care. Regular outreach via phone might also help drive engagement.

Patients in the struggling and detached segment 150 can be overwhelmed and disengaged. Patients in the struggling and detached segment 150 may not be hopeful or goal oriented, nor in-control of their future. Patients in the struggling and detached segment 150 can struggle with self-care and this segment may have the most trouble understanding health information. Patients in the struggling and detached segment 150 are often diagnosed with depression (53%) and are the least engaged in regular healthy behaviors. Patients in the struggling and detached segment 150 can be younger and suffer from more conditions, including COPD, anxiety, depression, etc.

The output data 175 for the struggling and detached segment 150 can be generated regularly. For example, a provider can intentionally reach-out regularly and assign a dedicated central care coordinator to patients in the struggling and detached segment 150 to build trust, encourage, educate patients, and establish a consistent health routine. Patients in the struggling and detached segment 150 can receive regular and expansive communication (e.g., phone, mail, email, etc.) of available services or resources that might help patients in the struggling and detached segment 150 learn about benefits that are accessible to them anytime. The frequent communication with patients in the struggling and detached segment 150 can increase awareness that drives engagement once patients in the struggling and detached segment 150 are ready to engage.

Patients in the depressed but involved segment 150 can be challenged but engaged. Patients in the depressed but involved segment 150 can be hopeful and goal-oriented even though they may suffer from the most health conditions relative to the other segments 150. Nearly all of the patients in the depressed but involved segment 150 may be diagnosed with depression. Patients in the depressed but involved segment 150 may not be overwhelmed and may be fairly health literate. Patients in the depressed but involved segment 150 may be most likely to contact customer service relative to patients in the other segments 150. Patients in the depressed but involved segment 150 may be very engaged in healthy behaviors and seek information on their own. Patients in the depressed but involved segment 150 may be more educated, younger, and skew female. Patients in the depressed but involved segment 150 may have the most access to technology, including the Internet relative to the other segments 150. On average, patients in the depressed but involved segment 150 may pose the highest per person cost to a health care provider.

The output data 175 for the depressed but involved segment 150 can include providing access to therapists and mental wellness resources (such as support groups) as a core aspect of a care plan. Patients in the depressed but involved segment 150 may be likely to welcome new digital solutions as an additional way to track and manage their health. The output data 175 for the depressed but involved segment 150 can offer mental wellness services among a slate of benefits to help them feel seen. Also, patients of the depressed but involved segment 150 can consider communicating the availability of outside peer groups to help them find a supportive community.

Referring now to FIG. 3, a table 300 of example patient segments and values for each patient segment 150 for dimensions or features of the patient data 125 is shown. The table 300 can indicate levels of clinical capacity, health engagement, health status, and access. Patients classified into the patient segments 150 by the machine learning engine 145 may be associated with features or feature scores (e.g., of the patient data 125) corresponding to the values described in table 300. High, medium, or low feature scores can indicate values above, below, or between various thresholds, predefined thresholds, or dynamically defined thresholds. For example, a score that is low may be less than a first threshold. A score that is medium may be greater than the first threshold but less than a second threshold. A score that is high may be greater than the second threshold. Each feature of the patient data 125 (e.g., clinical capacity, health engagement, health status, access) may have a specific first, second, and third threshold specific to the particular feature.

For example, the patients in the independent and capable segment 150 may be associated with a clinical capacity score above a predefined value. Clinical capacity may indicate the capacity for a patient to utilize clinical support. Parameters such as patient outlook, patient ability and support, and patient health literacy can form a score for a clinical capacity. Patients in the independent and capable segment 150 can have a clinical capacity score greater than the other segments 150, e.g., the support seeking and engaged segment 150, the struggling and detached segment 150, and the depressed but involved segment 150. The patients in the independent and capable segment 150 may have a health engagement score greater than a first level but less than a second level. The health engagement score can be based on parameters such as whether the patient is goal-oriented, engagement levels of the patient, and adherence levels of the patient. Health engagement can indicate the level at which a patient is willing and able to engage with healthy habits, medical treatments, or treatment plans.

The health engagement score of the independent and capable segment 150 can be a medium level, i.e., less than a health engagement score of the support seeking and engaged segment 150 and the depressed but involved segment 150 but greater than a health engagement score for the struggling and detached segment 150. The patients in the independent and capable segment 150 can have a health status score that is greater than a first threshold but less than a second threshold. The health status score can be based on a number of conditions a patient has and/or the number of medical claims the patient has made. The score of the patients in the independent and capable segment 150 for health status can be medium relative to other segments. For example, the score of the health status for the independent and capable segment 150 can be less than ideal (e.g., for a health patient) but greater than patients in the struggling and detached segment 150 and the depressed but involved segment 150. Patients in the independent and capable segment 150 can have a level of access to resources that is greater than a particular level. The access to resources can indicate a level at which patients have access to technology devices (e.g., smartphones, laptops, desktop computers) or technology services e.g., the Internet. The level of access to resources can indicate a level at which patients have access to basic needs, food, shelter, transportation, etc. The patients in the independent and capable segment 150 can be high relative to the patients in the support seeking and engaged segment 150, the struggling and detached segment 150, and the depressed but involved segment 150.

Patients in the support seeking and engaged segment 150 can have a clinical capacity score greater than a first level but less than a second level. The score for the clinical capacity of the patients in the support seeking and engaged segment 150 can be less than the clinical capacity score for the patients of the independent and capable segment 150, greater than the clinical capacity score for the patients of the struggling and detached segment 150, and similar to the clinical capacity score of the patients of the depressed but involved segment 150.

Patients in the support seeking and engaged segment 150 can have a health engagement score greater than a level. The score for the health engagement of the patients in the support seeking and engaged segment 150 can be greater than the health engagement score for the patients of the independent and capable segment 150, greater than the health engagement score for the patients of the struggling and detached segment 150, and greater than the health engagement score of the patients of the depressed but involved segment 150.

Patients in the support seeking and engaged segment 150 can have a health status score greater than a first level but less than a second level. The score for the health status of the patients in the support seeking and engaged segment 150 can be similar to the health status score for the patients of the independent and capable segment 150, greater than the health status score for the patients of the struggling and detached segment 150, and greater than the health status score of the patients of the depressed but involved segment 150.

Patients in the support seeking and engaged segment 150 can have a health status score greater than a first level but less than a second level. The score for the health status of the patients in the support seeking and engaged segment 150 can be similar to the health status score for the patients of the independent and capable segment 150, greater than the health status score for the patients of the struggling and detached segment 150, and greater than the health status score of the patients of the depressed but involved segment 150.

Patients in the support seeking and engaged segment 150 can have an access score less than a level. The score for the access of the patients in the support seeking and engaged segment 150 can be less than to the access score for the patients of the independent and capable segment 150, less than the access score for the patients of the struggling and detached segment 150, and less than the access score of the patients of the depressed but involved segment 150.

Patients in the struggling and detached segment 150 can have a clinical capacity less than a level. The score for the clinical capacity of the patients in the struggling and detached segment 150 can be less than the clinical capacity for the patients of the independent and capable segment 150, less than the clinical capacity score for the patients of the support seeking and engaged segment 150, and less than the clinical capacity of the patients of the depressed but involved segment 150.

Patients in the struggling and detached segment 150 can have a health engagement score less than a level. The score for the health engagement of the patients in the struggling and detached segment 150 can be less than the health engagement for the patients of the independent and capable segment 150, less than the health engagement score for the patients of the support seeking and engaged segment 150, and less than the health engagement of the patients of the depressed but involved segment 150.

Patients in the struggling and detached segment 150 can have a health status score less than a level. The score for the health status of the patients in the struggling and detached segment 150 can be less than the health status for the patients of the independent and capable segment 150, less than the health status score for the patients of the support seeking and engaged segment 150, and similar to the health status of the patients of the depressed but involved segment 150.

Patients in the struggling and detached segment 150 can have an access score less than a first level and greater than a second level. The score for the access of the patients in the struggling and detached segment 150 can be less than the access score for the patients of the independent and capable segment 150, greater than the access score for the patients of the support seeking and engaged segment 150, and similar to the access score of the patients of the depressed but involved segment 150.

Patients in the depressed but involved segment 150 can have a clinical capacity less than a first level and greater than a second level. The score for the clinical capacity of the patients in the depressed but involved segment 150 can be less than the clinical capacity for the patients of the independent and capable segment 150, similar to the clinical capacity for the patients of the support seeking and engaged segment 150, and greater than the clinical capacity score of the patients of the struggling and detached segment 150.

Patients in the depressed but involved segment 150 can have a health engagement score greater than a level. The score for the health engagement of the patients in the depressed but involved segment 150 can be greater than the health engagement for the patients of the independent and capable segment 150, similar to the health engagement for the patients of the support seeking and engaged segment 150, and greater than the health engagement score of the patients of the struggling and detached segment 150.

Patients in the depressed but involved segment 150 can have a health status score less than a level. The score for the health status of the patients in the depressed but involved segment 150 can be less than the health status for the patients of the independent and capable segment 150, less than the health status for the patients of the support seeking and engaged segment 150, and less than the heal status score of the patients of the struggling and detached segment 150.

Patients in the depressed but involved segment 150 can have an access score less than a first level and greater than a second level. The score for the access of the patients in the depressed but involved segment 150 can be less than the access for the patients of the independent and capable segment 150, greater than the access for the patients of the support seeking and engaged segment 150, and similar to the access score of the patients of the struggling and detached segment 150.

Figure 4:
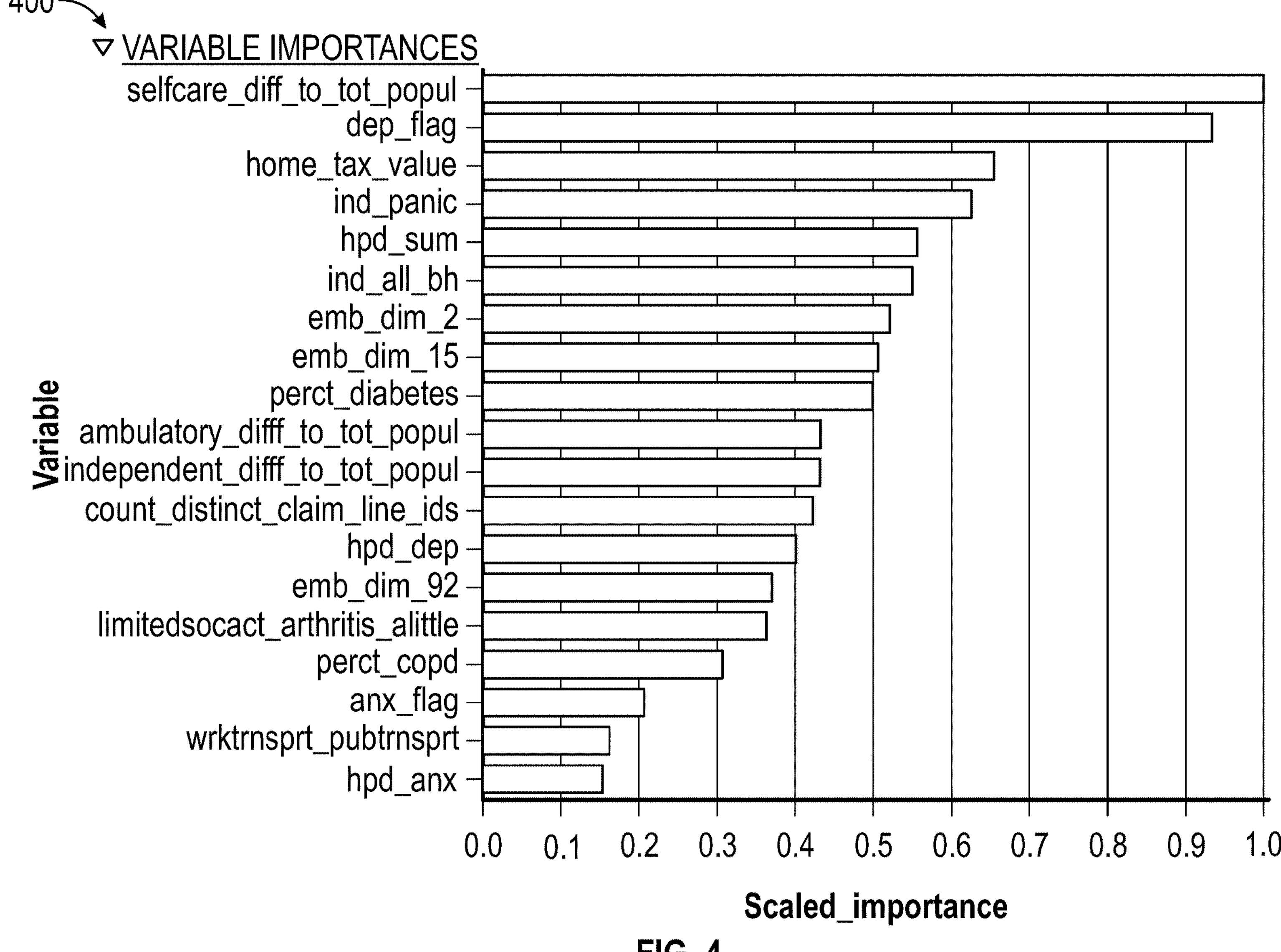
FIG. 4 is a table of example variable importance levels for variables of patient data.

Referring now to FIG. 4, a table 400 of example variable importance levels for variables of patient data 125 is shown. The machine learning engine 145 can generate the table 400 or generate the data included within the table 400. The machine learning engine 145 can use score features, variables, or parameters of the patient data 125 to determine a level of importance of the variables in predicting a particular outcome, e.g., whether a patient continues a treatment or stops a treatment. The importance level for the dimensions can indicate the level of importance of the variables in predicting a patient classification 155 of a patient into the patient segments 150. The machine learning engine 145 can use the variable importance levels to determine a subset of variables to use in classifying the patients into the patient segments 150. The machine learning engine 145 can use variables that are associated with importance levels over a threshold to construct, build, or generate the segments 150.

Figure 5:
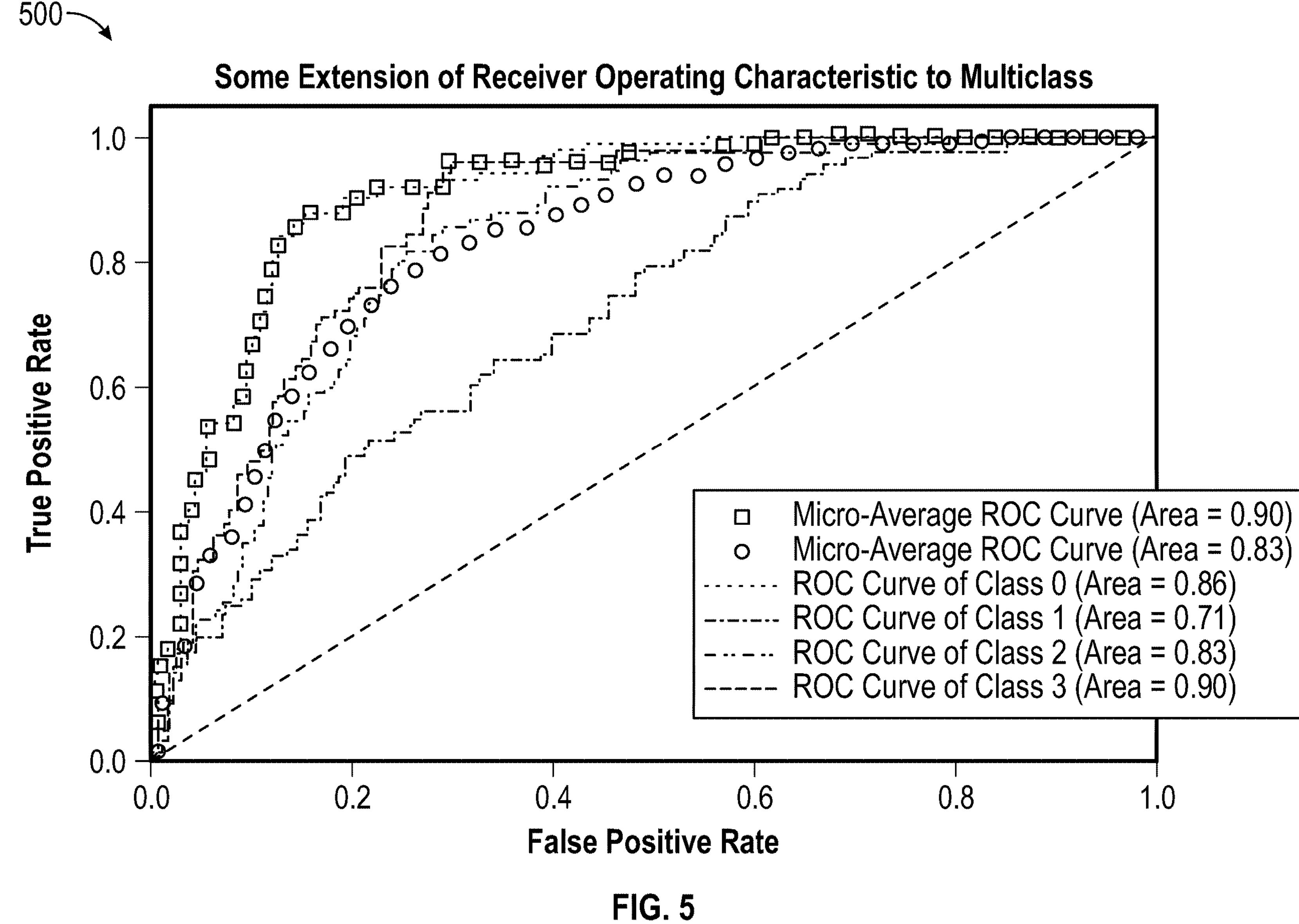
FIG. 5 is a chart of example receiver operating characteristics (ROCs) for a multiclass model.

Referring now to FIG. 5, a chart 500 of example receiver operating characteristic (ROCs) for a multiclass model executed by the machine learning engine 145 is shown. The machine learning engine can apply various parameters, thresholds, or values to the model and execute the model to classify patients in a dataset. The machine learning engine 145 can compute a true positive rate and a false positive rate for each class that the model classifies patients into. The true positive rate can be a measure of a probability that a classification of a patient into a particular class is correct. The false positive rate can be measure of a probability that a classification of a patient into the particular class is incorrect.

The chart 500 can plot the true positive rate and the false positive rate for multiple classes. For example, the chart 500 can plot the ROC curve for each patient segment 150. Furthermore, the machine learning engine 145 can determine an area under curve (AUC) for each ROC curve for each patient segment. The chart 500 can include an indication of AUC for each ROC curve for each patient segment. The area under each curve can indicate a performance, e.g., 86% for one class, 71% for another class, 83% for another class, and 90% for another class.

Figure 6:
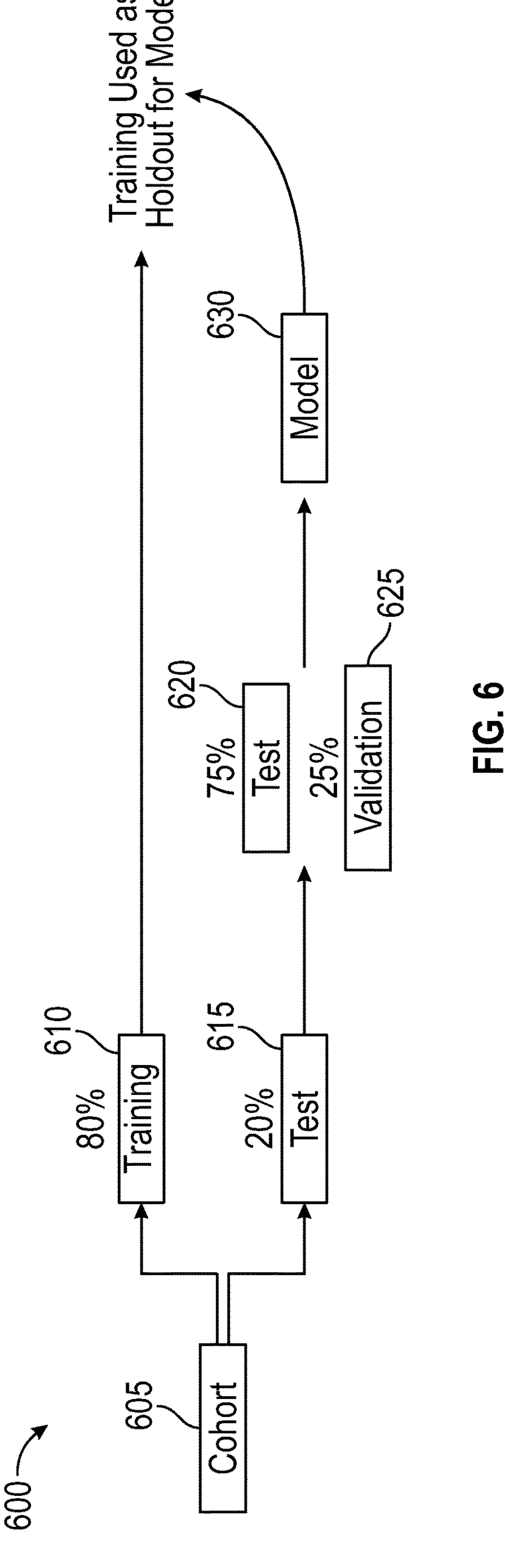
FIG. 6 is a block diagram of an example training and testing architecture for a model to classify patients into segments.

Referring now to FIG. 6, a block diagram of an example training and testing architecture 600 for a model 630 to classify patients into segments 150 is shown. The architecture 600 indicates a cohort 605. The cohort 605 can indicate the group, collection, or set of patients that the data processing system 105 has received patient data 125 for. The architecture 600 can indicate that 80% of the cohort 605 is assigned for model training while 20% of the cohort 605 is assigned for model testing. 70-90% of the cohort 605 can be assigned for model training. 65-95% of the cohort 605 can be assigned for model training. Less than 65% of the cohort 605 can be assigned for model training. More than 95% of the cohort 605 can be assigned for model training. 15-25% of the cohort 605 can be assigned for model testing. 10-30% of the cohort 605 can be assigned for model testing. Less than 10% of the cohort 605 can be assigned for model testing. More than 30% of the cohort 605 can be assigned for model testing.

The machine learning engine 145 can train the model 630 based on the patients of the training set 610. The machine learning engine 145 can further subdivide the testing set 615 into a testing set 620 and a validation set 625. 75% of the testing set 615 can be selected for the testing set 620. 25% of the testing set 615 can be selected for the validation set 625. 70-80% of the testing set 615 can be selected for the testing set 620. 65-85% of the testing set 615 can be selected for the testing set 620. Less than 65% of the testing set 615 can be selected for the testing set 620. More than 85% of the testing set 615 can be selected for the testing set 620. 20-30% of the testing set 615 can be selected for the validation set 625. 15-35% of the testing set 615 can be selected for the validation set 625. Less than 15% of the testing set 615 can be selected for the validation set 625. More than 35% of the testing set 615 can be selected or the validation set 625. The testing set 620 and the validation set 625 can be used by the machine learning engine 145 to train and validate the model 630. The training set 610 can be used as a holdout set for the model 630.

Figure 7A:
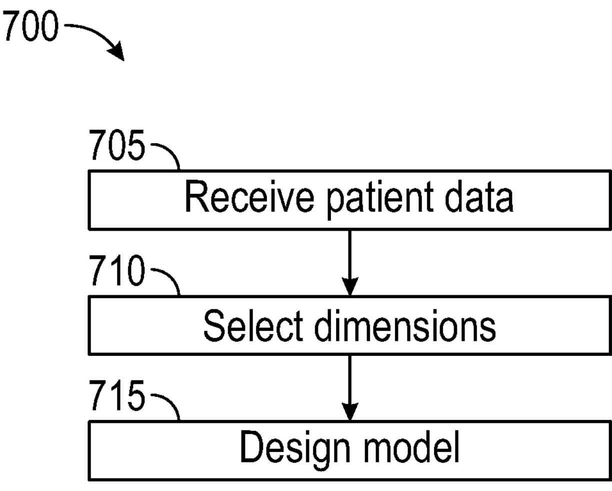
FIG. 7A is an example method of designing a machine learning model for classifying patients into segments.

FIG. 7A is an example method 700 of designing a machine learning model for classifying patients into segments. The method 700 can be performed by the data processing system 105. For example, at least one step, or a portion of one step of the method 700, can be performed by the user interface manager 130, the machine learning engine 145, the patient database 160, or the output generator 170. The method 700 can be performed by the patient device 115 or the medical device 120. The method 700 can include a step 705 of receiving patient data. The method 700 can include a step 710 of selecting dimensions. The method 700 can include a step 715 of designing a model.

In step 705, the method 750 can include receiving the patient data 125. The data processing system 105 can receive the patient data 125. The user interface manager 130 can generate a questionnaire and deliver the questionnaire to the patient device 115 or conduct the questionnaire. The answers a patient provides via the patient device 115 can be or be included in the patient data 125.

In step 710, the method 750 can include selecting, by the data processing system 105, dimensions 140. The machine learning engine 145 can identify importance levels of various dimensions, features, parameters, or value categories of the patient data 125. The key features identified for training the model can be related to domains around independence, self-care, depression, diagnostic and statistical manual of mental discovers (DSM-V) diagnoses, home value, and claims usage. The importance level of the dimensions can indicate a correlation between the dimension and another feature, e.g., a target or goal. The importance level can indicate a correlation between a dimension and a patient continuing or dropping out of a medical treatment. Furthermore, if the segments 150, or a first version of iteratively determined segments 150, are already generated by the machine learning engine 145, the importance level can indicate a correlation between the dimension and classifications of the patients into the segments 150.

In step 715, the method 750 can include designing, by the data processing system 105, a model. For example, the data processing system 105 can generate the segments 150 based on the dimensions 140. The machine learning engine 145 can generate the patient segments 150 based on identifying significant combinations of values of the dimensions 140. The machine learning engine 145 can receive user input from a user device that indicates or selects values of the dimensions 140 that indicate the segments 150. The data processing system 105 can design or configure a model to receive the dimensions 140 as inputs and output the patient classifications 155 according to the segments 150.

Figure 7B:
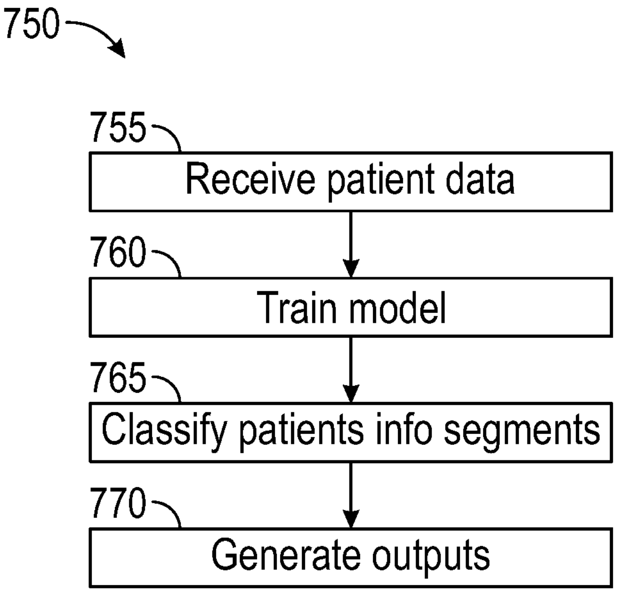
FIG. 7B is an example method of classifying patients into segments based on machine learning.

FIG. 7B is an example method 750 of classifying patients into segments based on machine learning. The method 750 can be performed by the data processing system 105. For example, at least one step, or a portion of one step of the method 750, can be performed by the user interface manager 130, the machine learning engine 145, the patient database 160, or the output generator 170. The method 700 can be performed by the patient device 115 or the medical device 120.

The method 750 can include a step 755 of receiving patient data. The method 700 can include a step 760 of training a model. The method 750 can include a step 765 of classifying patients into segments. The method 750 can include a step 770 of generating an output.

In step 755, the method 750 can include receiving the patient data 125. The data processing system 105 can receive the patient data 125. For example, the data processing system 105 can receive, collect, identify, the patient data 125 from the external database 110 or the patient device 115. For example, the user interface manager 130 can query the external database 110 for the patient data 125.

In step 760, the method 750 can include training a model. The machine learning engine 145 can train a model of the machine learning engine 145 to generate a patient classification 155 for at least one patient based on patient data 125 for the patient. The model can be the model designed in FIG. 7A. The machine learning engine 145 can execute at least one learning process to identify parameters for the model that causes the model to classify patients into the patient segments 150. The machine learning engine 145 can train the model based on training data that can include patient data 125 and a corresponding patient classification 155 for the patient segment. The training data can be labeled by a user, in some examples.

In step 765, the method 750 can include classifying patients into the segments 150. The machine learning engine 145 can generate a prediction that the patient belongs to each of the patient segments 150. The machine learning engine 145 can generate a patient classification 155 for the patient by selecting a patient segment 150 associated with a highest prediction. In step 770, the method 750 can include generating outputs. The output generator 170 can generate output data 175 based on the patient classifications 155. For example, the output generator 170 can generate content for a particular patient based on the segment 150 that the patient is classified into. The content can be an email, a message, a notification, images, etc.

Figure 8:
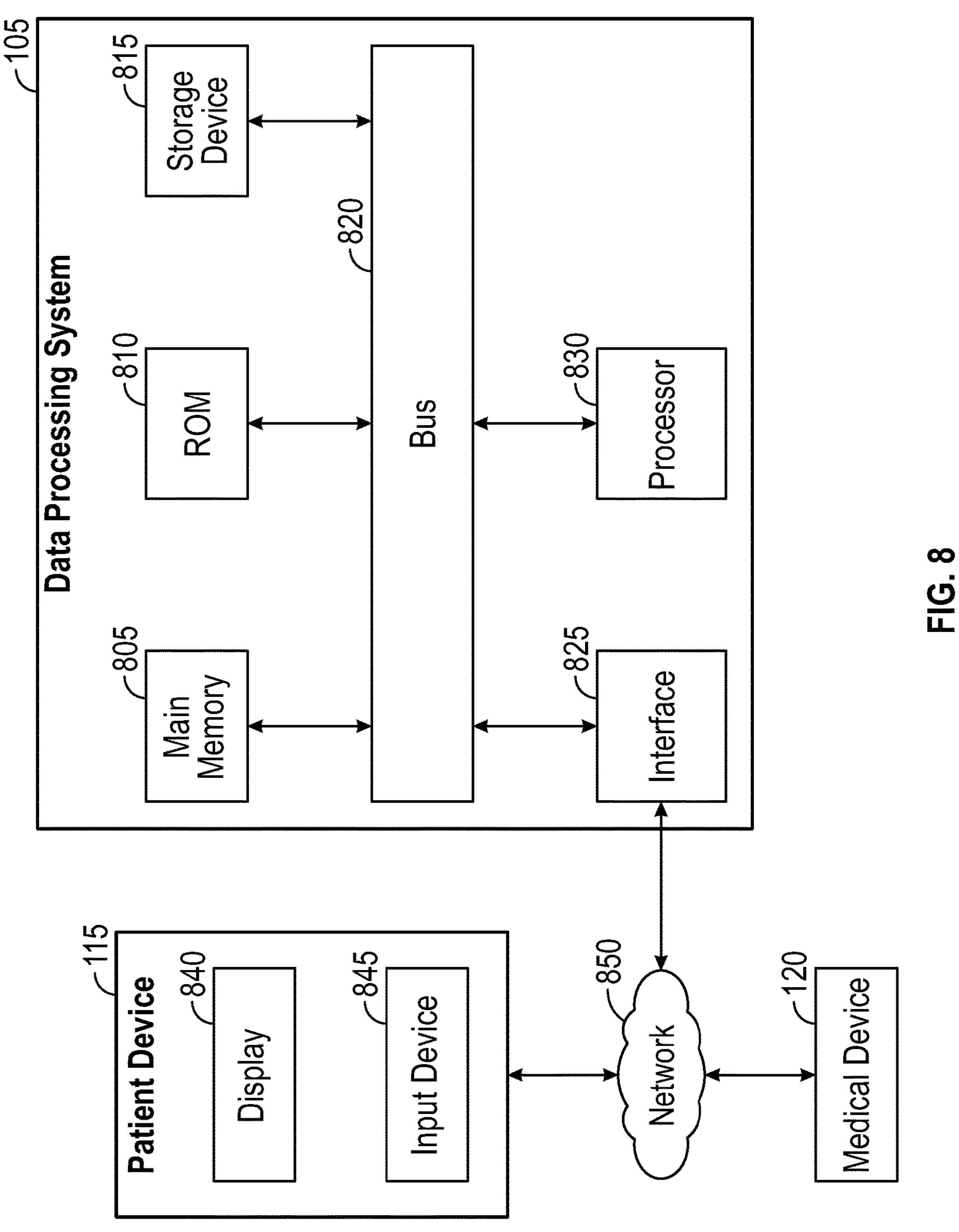
FIG. 8 is a block diagram of a data processing system.

Referring now to FIG. 8, a data processing system 105 is shown that can be used, for example. The computing architecture described in FIG. 8 can be used for the data processing system 105, the patient device 115, or the medical device 120. The data processing system 105 includes a bus 820 or other communication component for communicating information and a processor 830 coupled to the bus 820 for processing information. The data processing system 105 also includes main memory 805, such as a random access memory (RAM) or other dynamic storage device, coupled to the bus 820 for storing information, and instructions to be executed by the processor 830. Main memory 805 can also be used for storing position information, temporary variables, or other intermediate information during execution of instructions by the processor 830. The data processing system 105 may further include a read only memory (ROM) 810 or other static storage device coupled to the bus 820 for storing static information and instructions for the processor 830. A storage device 815, such as a solid state device, magnetic disk or optical disk, is coupled to the bus 820 for persistently storing information and instructions.

The data processing system 105 may be coupled via the bus 820 to a display 840, such as a liquid crystal display, or active matrix display, for displaying information to a user. The display 840 can be a display of the patient device 115. An input device 845, such as a keyboard including alphanumeric and other keys, may be coupled to the bus 820 for communicating information, and command selections to the processor 830. The input device 845 can be a component of the patient device 115. In another implementation, the input device 845 has a touch screen display 840. The input device 845 can include a cursor control, such as a mouse, a trackball, or cursor direction keys, for communicating direction information and command selections to the processor 830 and for controlling cursor movement on the display 840.

In some implementations, the data processing system 105 may include an interface 825, such as a networking adapter. The interface 825 may be coupled to bus 820 and may be configured to enable communications with a computing or communications network 850 and/or other computing systems, e.g., the patient device 115 or the medical device 120. In various illustrative implementations, any type of networking configuration may be achieved using interface 825, such as wired (e.g., via Ethernet), wireless (e.g., via Wi-Fi, Bluetooth, etc.), pre-configured, ad-hoc, LAN, WAN, etc.

According to various implementations, the processes that effectuate illustrative implementations that are described herein can be achieved by the data processing system 105 in response to the processor 830 executing an arrangement of instructions contained in main memory 805. Such instructions can be read into main memory 805 from another computer-readable medium, such as the storage device 815. Execution of the arrangement of instructions contained in main memory 805 causes the data processing system 105 to perform the illustrative processes described herein. One or more processors in a multi-processing arrangement may also be employed to execute the instructions contained in main memory 805. In alternative implementations, hard-wired circuitry may be used in place of or in combination with software instructions to implement illustrative implementations. Thus, implementations are not limited to any specific combination of hardware circuitry and software.

Although an example processing system has been described in FIG. 8, implementations of the subject matter and the functional operations described in this specification can be carried out using other types of digital electronic circuitry, or in computer software, firmware, or hardware, including the structures disclosed in this specification and their structural equivalents, or in combinations of one or more of them.

The construction and arrangement of the systems and methods as shown in the various exemplary examples are illustrative only. Although only a few examples have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative examples. Other substitutions, modifications, changes, and omissions may be made in the design, operating conditions and arrangement of the exemplary examples without departing from the scope of the present disclosure.

The present disclosure contemplates methods, systems and program products on any machine-readable media for accomplishing various operations. The examples of the present disclosure may be implemented using existing computer processors, or by a special purpose computer processor for an appropriate system, incorporated for this or another purpose, or by a hardwired system. Examples within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

In various implementations, the steps and operations described herein may be performed on one processor or in a combination of two or more processors. For example, in some implementations, the various operations could be performed in a central server or set of central servers configured to receive data from one or more devices (e.g., edge computing devices/controllers) and perform the operations. In some implementations, the operations may be performed by one or more local controllers or computing devices (e.g., edge devices), such as controllers dedicated to and/or located within a particular building or portion of a building. In some implementations, the operations may be performed by a combination of one or more central or offsite computing devices/servers and one or more local controllers/computing devices. All such implementations are contemplated within the scope of the present disclosure. Further, unless otherwise indicated, when the present disclosure refers to one or more computer-readable storage media and/or one or more controllers, such computer-readable storage media and/or one or more controllers may be implemented as one or more central servers, one or more local controllers or computing devices (e.g., edge devices), any combination thereof, or any other combination of storage media and/or controllers regardless of the location of such devices.

A number of implementations have been described. Nevertheless, it will be understood that additional modifications may be made without departing from the scope of the inventive concepts described herein, and, accordingly, other examples are within the scope of the following claims.

What is claimed:

1. A system comprising one or more memory devices having instructions stored thereon, that, when executed by one or more processors, cause the one or more processors to:

receive data of dimensions of a plurality of patients from one or more data sources;

select a portion of the dimensions based on a level at which the dimensions predict that a patient will stop a treatment;

determine a plurality of segments, wherein the plurality of segments describe at least one of an attitude towards healthcare or an independence relative to a healthcare provider;

classify the plurality of patients into the plurality of segments based on execution of a model trained based on a machine learning process and based on the data of the selected portion of the dimensions;

construct a database;

update the database to store classifications of the plurality of patients into the plurality of segments;

construct output data based on the classifications of the plurality of patients into the plurality of segments stored in the database;

select a software application from a plurality of software applications for the patient based on a segment into which the model classified the patient;

generate at least one credential for the patient to access the software application;

construct a message to access the software application, the message comprising the at least one credential or a link to accessing the software application with the at least one credential; and transmit the message to a device of the patient.

2. The system of claim 1, wherein the instructions cause the one or more processors to:

generate a training data set based on the data, the training data set comprising:

a plurality of sets of the data for a portion of the plurality of patients; and segments that the portion of the plurality of patients are classified into; and train the model by execution of the machine learning process on the training data set.

3. The system of claim 1, wherein the instructions cause the one or more processors to:

retrieve, from the database, a classification of a first patient of the plurality of patients into a first segment of the plurality of segments;

retrieve, from the database, a classification of a second patient of the plurality of patients into a second segment of the plurality of segments;

generate first output data for the first patient based on the classification of the first patient into the first segment; and generate second output data for the second patient based on the classification of the second patient into the second segment, wherein the first output data is different than the second output data.

4. The system of claim 1, wherein the instructions cause the one or more processors to:

retrieve, from the database, a classification of the patient of the plurality of patients into the segment of the plurality of segments;

select the software application for the patient from the database, the software application linked to the segment;

generate the output data to provide the patient access to the software application; and transmit the output data to the device of the patient.

5. The system of claim 1, wherein the instructions cause the one or more processors to:

execute a second machine learning process based on the data to identify a level that the dimensions of the data stored in the database predict that the patient will stop the treatment;

identify the portion of the dimensions associated with levels greater than a threshold; and construct the plurality of segments based on the portion of the dimensions.

6. The system of claim 1, wherein the instructions cause the one or more processors to:

construct the database to include a plurality of sections;

save first data of the data describing the plurality of patients in a first section of the plurality of sections linked to a first segment of the plurality of segments;

store at least one identifier of the first segment in the database to label the first data stored in the first section;

save second data of the data describing the plurality of patients in a second section of the plurality of sections linked to a second segment of the plurality of segments; and store at least one identifier of the second segment in the database to label the second data stored in the second section.

7. The system of claim 6, wherein the instructions cause the one or more processors to:

receive a request to generate an output for patients classified into the first segment;

query the database based on the at least one identifier for the first segment;

receive the first data responsive to the query; and execute an operation to generate the output for the patients based on the first data received from the database.

8. A method, comprising:

receiving, by one or more processing circuits, data of dimensions of a plurality of patients from one or more data sources;

executing, by the one or more processing circuits, a first machine learning process based on the data to identify a level that the dimensions of the plurality of patients of the data predict that patients will stop a treatment;

selecting, by the one or more processing circuits, a portion of the dimensions associated with levels greater than a threshold;

constructing, by the one or more processing circuits, a plurality of segments based on the portion of the dimensions, wherein the plurality of segments describe at least one of an attitude towards healthcare or an independence relative to a healthcare provider;

classifying, by the one or more processing circuits, the plurality of patients into the plurality of segments based on execution of a model trained based on a second machine learning process and based on the data of the selected portion of the dimensions;

constructing, by the one or more processing circuits, a database;

updating, by the one or more processing circuits, the database to store classifications of the plurality of patients into the plurality of segments; and constructing, by the one or more processing circuits, output data based on the classifications of the plurality of patients into the plurality of segments stored in the database.

9. The method of claim 8, comprising:

generating, by the one or more processing circuits, a training data set based on the data, the training data set comprising:

a plurality of sets of the data for a portion of the plurality of patients; and segments that the portion of the plurality of patients are classified into; and training, by the one or more processing circuits, the model by execution of the second machine learning process on the training data set.

10. The method of claim 9, comprising:

selecting, by the one or more processing circuits, a software application from a plurality of software applications for a patient based on a segment into which the model classified the patient;

generating, by the one or more processing circuits, at least one credential for the patient to access the software application;

constructing, by the one or more processing circuits, a message to access the software application, the message comprising the at least one credential or a link to accessing the software application with the at least one credential; and transmitting, by the one or more processing circuits, the message to a device of the patient.

11. The method of claim 8, comprising:

retrieving, by the one or more processing circuits, from the database, a classification of a first patient of the plurality of patients into a first segment of the plurality of segments;

retrieving, by the one or more processing circuits, from the database, a classification of a second patient of the plurality of patients into a second segment of the plurality of segments;

generating, by the one or more processing circuits, first output data for the first patient based on the classification of the first patient into the first segment; and generating, by the one or more processing circuits, second output data for the second patient based on the classification of the second patient into the second segment, wherein the first output data is different than the second output data.

12. The method of claim 8, comprising:

retrieving, by the one or more processing circuits, from the database, a classification of a patient of the plurality of patients into a segment of the plurality of segments;

selecting, by the one or more processing circuits, at least one software application for the patient from the database, the at least one software application linked to the segment;

generating, by the one or more processing circuits, the output data to provide the patient access to the at least one software application; and transmitting, by the one or more processing circuits, the output data to a device of the patient.

13. The method of claim 9, comprising:

constructing, by the one or more processing circuits, the database to include a plurality of sections;

saving, by the one or more processing circuits, first data of the data describing the plurality of patients in a first section of the plurality of sections linked to a first segment of the plurality of segments;

storing, by the one or more processing circuits, at least one identifier of the first segment in the database to label the first data stored in the first section;

saving, by the one or more processing circuits, second data of the data describing the plurality of patients in a second section of the plurality of sections linked to a second segment of the plurality of segments; and storing, by the one or more processing circuits, at least one identifier of the second segment in the database to label the second data stored in the second section.

14. The method of claim 13, comprising:

receiving, by the one or more processing circuits, a request to generate an output for patients classified into the first segment;

querying, by the one or more processing circuits, the database based on the at least one identifier for the first segment;

receiving, by the one or more processing circuits, the first data responsive to the query; and executing, by the one or more processing circuits, an operation to generate the output for the patients based on the first data received from the database.

15. One or more storage media having instructions stored thereon, that, when executed by one or more processors, cause the one or more processors to:

receive data of dimensions of a plurality of patients from one or more data sources;

select a portion of the dimensions based on a level at which the dimensions predict that a patient will stop a treatment;

determine a plurality of segments, wherein the plurality of segments describe at least one of an attitude towards healthcare or an independence relative to a healthcare provider;

classify the plurality of patients into the plurality of segments based on execution of a model trained based on a machine learning process and based on the data of the selected portion of the dimensions;

construct a database, the database including a plurality of sections;

update the database to store classifications of the plurality of patients into the plurality of segments by:

saving first data of the data describing the plurality of patients in a first section of the plurality of sections linked to a first segment of the plurality of segments;

storing at least one identifier of the first segment in the database to label the first data stored in the first section;

saving second data of the data describing the plurality of patients in a second section of the plurality of sections linked to a second segment of the plurality of segments; and storing at least one identifier of the second segment in the database to label the second data stored in the second section; and construct output data based on the classifications of the plurality of patients into the plurality of segments stored in the database.

16. The one or more storage media of claim 15, wherein the instructions cause the one or more processors to:

generate a training data set based on the data, the training data set comprising:

a plurality of sets of the data for a portion of the plurality of patients; and segments that the portion of the plurality of patients are classified into; and train the model by execution of the machine learning process on the training data set.

17. The one or more storage media of claim 15, wherein the instructions cause the one or more processors to:

select a software application from a plurality of software applications for a patient based on a segment into which the model classified the patient;

generate at least one credential for the patient to access the software application;

construct a message to access the software application, the message comprising the at least one credential or a link to accessing the software application with the at least one credential; and transmit the message to a device of the patient.

18. The one or more storage media of claim 15, wherein the instructions cause the one or more processors to:

execute a second machine learning process based on the data to identify a level that the dimensions of the data stored in the database predict that the patient will stop the treatment;

identify the portion of the dimensions associated with levels greater than a threshold; and construct the plurality of segments based on the portion of the dimensions.

* * * * *